United States Patent [19]
Van Geenen et al.

[11] Patent Number: 4,683,304
[45] Date of Patent: Jul. 28, 1987

[54] PROCESS FOR PREPARING AN ACYL-LACTAM COMPOUND

[75] Inventors: Albert A. Van Geenen, Brunssum; Jozef J. M. Bongers, Elsloo, both of Netherlands

[73] Assignee: Stamicarbon B.V., Geleen, Netherlands

[21] Appl. No.: 808,560

[22] Filed: Dec. 13, 1985

[30] Foreign Application Priority Data

Dec. 20, 1984 [NL] Netherlands ............ 8403862

[51] Int. Cl.$^4$ .................. C07D 223/10; C07D 211/40; C07D 209/34
[52] U.S. Cl. .................................... 540/529; 546/222; 546/243; 548/538; 548/540; 528/315
[58] Field of Search ................. 260/239.3 R; 546/243, 546/221; 548/538, 540; 540/529

[56] References Cited

U.S. PATENT DOCUMENTS 4,626,385 12/1986 Ashida et al. .............. 546/243

Primary Examiner—Robert T. Bond
Attorney, Agent, or Firm—Cushman, Darby & Cushman

[57] ABSTRACT

The invention relates to a process for preparing an acyl-lactam compound characterized in that the reaction product of a lactam with a dicarboxylic acid anhydride is reacted with a polyol at a temperature of 150° C. at most. These acyl-lactam compounds are very suitable as activator in the preparation of nylon block copolymers, more specifically in the RIM or RRIM systems.

5 Claims, No Drawings

PROCESS FOR PREPARING AN ACYL-LACTAM COMPOUND

FIELD OF THE INVENTION

The invention relates to a process for preparing an acyllactam compound. In the anionic polymerization of lactams such as caprolactam acyl-lactam compounds are suitable accelerators. Particularly in the preparation of RIM (=Reaction Injection Moulding) nylon can these compounds be used on account of the short time required for their reaction, which makes it possible for lactam to be polymerized in a mould.

BACKGROUND OF THE PRESENT INVENTION

The RIM preparation process is a one-step process in which the liquid components are put in a mould, upon which a very rapid polymerization takes place resulting in a plastic article. The pressures applied in that process are much lower than in the much used injection moulding process.

In a RIM preparation process the viscosity of the components put in the moulds is 50 to 10,000 cps, preferably about 1000–3000 cps. In that process the temperature of the components ranges from room temperature for urethanes to about 100°–150° C. for lactams. The mould temperature in a RIM preparation process for lactam is usually between 100° and 220° C. The pressures applied range from 1 to 100 bar, preferably from 1 to 30 bar.

For smaller articles the reaction in the mould must be finished in less than 5 minutes.

The polymerization of a lactam to form nylon has been known for long.

In the U.S. Pat. No. 3,018,273 a process for the anionic polymerization of caprolactam is described using an organomagnesium compound as catalyst and an N—N diacyl compound as activator.

The British Pat. No. 1,067,153 describes a process for preparing nylon block copolymers by polymerizing caprolactam in the presence of various kinds of activators. In the example the use of an isocyanate-terminated polypropylene glycol as activator and of a potassium compound as catalyst is described.

In the U.S. Pat. Nos. 3,862,262, 4,031,164, 4,034,015, 4,223,112, 3,925,325 and 3,965,075, as well as U.S. Pat. Re. No. 30,371, various aspects of the preparation of activators for the polymerization of lactam and of the polymerization of lactam itself are described.

The U.S. Pat. Nos. 4,031,164 and 4,223,112 describe lactam-polyol-polyacyl-lactam block copolymers with specific ratios of the various components.

The U.S. Pat. No. 3,862,262 describes lactam-polyol-acyl-polylactam block copolymers.

The U.S. Pat. No. 4,034,015 aims at nylon block copolymers with at least 5% ester end groups.

The other patents mentioned relate to the preparation of ester-amide compounds by condensation of alcohol and acyl-lactam in the presence of various kinds of catalysts.

The European patent applications Nos. 67693, 67694, 67695 laid open to public inspection relate to acyl-halide and acyl-lactam compounds and to a process for preparing nylon block copolymers with these.

The acyl-halide and acyl-lactam compounds are described by means of complex formulas.

The U.S. Pat. No. 3,366,608 describes the reaction of an N, N'diacyl-bis caprolactam, such as N, N'sebacoyl-bis-caprolactam, a polyol and a basic catalyst. In that process a nylon block copolymer is obtained.

The German patent application No. 2026672 laid open to public inspection describes the use of polyol-containing polyamides for the production of metallized articles. The polyol-containing polyamides are obtained by anionic polymerization of lactam in the presence of a polyol, a basic lactam catalyst and an activator, such as a diisocyanate.

The U.S. Pat. No. 4,540,516 describes the preparation of N-substituted carbamoyl-lactam compounds, while the U.S. Pat. No. 4,540,515 describes the use of such a compound for the preparation of nylon block copolymers.

The European patent application No. 147792 describes the catalytic condensation of imides and alcohols to form esteracyllactam and esteramide-acyl-lactam compounds.

In the U.S. Pat. No. 3,704,280 a process is described for the anionic catalytic polymerization of lactam in the presence of a polyether, in which process the activator used is an isocyanate compound.

The invention relates to processes for preparing acyl lactam compounds comprising reacting a poyol and the reaction product of a lactam and dicaboxylic acid anhydride at a temperature of at most 150° C.

The compounds produced by the process are very suitable for use as activators in the preparation of nylon block copolymers, and more specifically in RIM or RRIM systems.

SUMMARY OBJECTS OF THE PRESENT INVENTION

The present invention provides a novel process for preparing an acyl-lactam compound that can well be used, inter alia, as an accelerator for anionic polymerization of lactam as may be applied, for instance, in (rotational) moulding of nylon. The present invention thus also provides a novel acyl-lactam compound capable of producing nylon block copolymers with good properties, particularly via 'Reaction Injection Moulding'.

DETAILED DESCRIPTION OF THE PRESENT INVENTION

The process according to the invention is characterized in that a polyol is reacted with the reaction product of a dicarboxylic acid anhydride with a lactam, preferably in a liquid or dissolved state, at a temperature of 150° C. at most. Preferably at a temperature between 60° C. and 140° C. and more preferably between 80° and 130° C.

The reaction product (I) of a lactam with a dicarboxylic acid anhydride is understood to comprise compounds with the formula

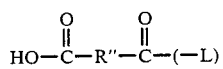

where
R'' is a bivalent radical having the following general formula

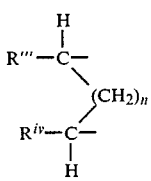

wherein
R''' is H, alkyl, cycloalkyl, aryl, alkaryl or aralkyl,
R$^{iv}$ is H, alkyl, cycloalkyl, aryl, alkaryl or aralkyl where
R''' and R$^{iv}$ may jointly form a substituted or non-substituted cycloalkyl residue
n is 0 or 1 and
(-L) represents a non-opened lactam ring of the formula:

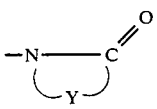

wherein Y is a hydrocarbon residue with 3–11 carbon atoms.

This reaction product (I) is formed when a suitable dicarboxy-lic acid anhydride and a lactam are reacted with each other in a liquid state at a temperature of 150° C. at most, preferably at a temperature between 70° C. and 140° C. and more preferably between 90° C. and 130° C. Liquid state is understood to mean a mixture of two liquids as well as a solid component dissolved in a liquid component. In this reaction process it is in principle assumed that virtually all anhydride groups have reacted with a lactam molecule.

If the reaction product (I) is reacted with a polyol, preferably in the presence of a substance promoting the esterification, compounds will be formed having the following formula

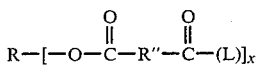

where:
R represents a polyol residue originating from a polyol with the formula R—(OH)$_x$
where x is a number $\geq 2$
R'' is a bivalent radical having the following general formula

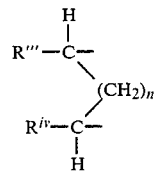

wherein
R''' is H, alkyl, aryl, alkaryl, aralkyl or cycloalkyl
R$^{iv}$ is H, alkyl, aryl, alkaryl, aralkyl or cycloalkyl where
R''' and R$^{iv}$ may jointly form a substituted or non-substituted cycloalkyl residue, and
n is 0 or 1.

It has been found that this group of compounds is very suitable as activator in the preparation of nylon block copolymers, more specifically in the so-called RIM (Reaction Injection Moulding) or RRIM (reinforced RIM) systems, in which it is highly essential for the polymerization to take effect within a very short time.

Morever, using these compounds highly impact-resistance articles can be made from nylon block copolymers.

The polyol applied may in principle be any polyol, but on the grounds of the mechanical properties to be obtained preference is given to rubber-like polyols with an equivalent weight of at least 300, more specifically from 1000 to 5000. Beyond an equivalent weight of 5000 the properties of the nylon block copolymer may deteriorate.

Suitable polyols are polyether polyols, polyester polyols, polybutadiene polyols, siloxane-containing polyols and/or the so-called 'polymeric' polyols. These 'polymeric' polyols comprise polyols grafted with, for instance, acrylonitrile or a mixture of styrene and acrylonitrile, but also the polyurea dispersions obtained by reacting equivalent amounts of diamine or hydrazine with diisocyanate dissolved in the polyol.

The concepts of molecular weight and equivalent weight as used herein relate to the number-average molecular weight.

The concept of equivalent weight of a polyol relates to the number-average molecular weight of the polypol per hydroxyl group i.e. the molecular weight divided by the functionality. Mixtures of two or more polyols may be used also.

As lactam various lactams may be used, such as 2-pyrrolidone, 2-piperidone, enantholactam, decanolactam, undecanolactam, lauryllactam and caprolactam, but also substituted lactams, or mixtures of two or more lactams. More specifically caprolactam is used.

The dicarboxylic acid anhydrides to be used are chosen from the group of dicarboxylic acid anhydrides having the following general formula

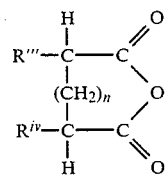

wherein
R''' represents H, alkyl, cycloalkyl, aryl, alkaryl or aralkyl
R$_{iv}$ is H, alkyl, cycloalkyl, aryl, alkaryl or aralkyl where
R''' and R$_{iv}$ may jointly form a substituted or non-substituted cycloalkyl residue, and
n is 0 or 1.

Very suitable are dicarboxylic acid anhydrides, such as glutaric acid anhydride, succinic acid anhydride, and saturated alicyclic 1,2 dicarboxylic acid anhydrides, such as 1,2 cyclohexanedicarboxylic anhydride.

Applicant has found that compounds like maleic acid anhydride and phthalic acid anhydride cannot be used in the present invention.

As substances promoting the esterification of the polyol with reaction product I esterification catalysts may be used. Very suitable are highly dehydrating substances such as carbodiimides, for instance diphenylcarbodiimide. Sometimes it is desirable for these compounds to be applied in stoichiometric amounts.

The present invention also relates to a process for preparing a nylon block copolymer, as well as to an article wholly or partly produced from such a nylon block copolymer.

This process is characterized in that an acyl-lactam compound described above is reacted in melted lactam to form a nylon block copolymer in the presence of a lactam polymerization catalyst. Preference is given to carrying out the reaction with an alkali or alkaline earth metal lactamate or with compounds forming alkali or alkaline earth metal lactamate. Examples thereof include sodium lactamate, potassium lactamate and lactam magnesiumbromide. Already a small amount of catalyst will suffice, for instance less than 1 mole % calculated on the lactam to be polymerized, but larger amounts, to for instance 3 moles % can also be used. Preferably the amount of catalyst is between 0.2 and 3 moles %.

The block copolymer is formed in a short time, for instance in less than 10 minutes, more specifically between 10 s. and 5 minutes, under mild conditions in respect of temperature and pressure.

The proportions between lactam monomer and acyl lactam may vary within wide limits. These proportions are generally between 5 and 95% (wt) of each of the components. In order to obtain suitable impact-resistance articles having a reasonable hardness and rigidity preference is given to 5–40% (wt) acyl-lactam compound calculated on the total mixture. More specifically 10–30% (wt) acyl-lactam compound is used.

In the preparation of nylon block copolymer the object is for the number-average molecular weight of the nylon blocks to be at least 2000, more specifically at least 4000. This can be achieved by varying the number of acyl-lactam groups originating from the acyl-lactam compound in respect of the amount of lactam added.

The chosen lactam added for preparing the nylon block copolymer is preferably the same as used in the acyl-lactam compound. More specifically caprolactam is used.

In the preparation of the nylon block copolymer it may be essential for the polymerization to be carried out in the presence of one or more compounds that are normally used in nylon block copolymers, such as fillers, softeners, flame-retardants, stabilizers and rein-forcing fibres, such as asbestos or glass fibres.

The present invention is elucidated hereinafter by means of a few examples.

EXAMPLE 1

11.4 g (0.1 mole) glutaric acid anhydride and 11.3 g (0.1 mole) ε-caprolactam were reacted for 4 hours at 125° C.

To the reaction product formed 200 g (0.5 mole) polypropylene glycol (molecular mass 4000) and 19.4 (0.1 mole) diphenylcarbodiimide were subsequently added. After stirring for 2 hours at 125° C. the whole was cooled to 60° C. and the diphenylurea formed from the diphenylcarbodiimide was filtered off.

8.8 g of the product formed was dissolved at 100° C. in 13 g caprolactam. After addition of this solution to 0.5 g lactam magnesiumbromide in 17.7 g caprolactam a solid nylon polymer was obtained herefrom in 3 min. and 10 seconds.

EXAMPLE 2

10 g (0.1 mole) succinic acid anhydride and 11.3 g (0.1 mole) ε-caprolactam were reacted for 4 hours at 125° C.

To the reaction product formed 200 g (0.5 mole) polypropylene glycol (molecular mass 4000) and 19.4 g (0.1 mole) diphenylcarbodiimide were subsequently added. After stirring for 2 hours at 125° C. the whole was cooled to 60° C. and the diphenylurea formed from the diphenylcarbodiimide was filtered off.

11 g of the product formed was dissolved at 100° C. in 13 g caprolactam. After addition of this solution to 0.6 g lactam magnesiumbromide in 15.4 g caprolactam a solid nylon polymer was formed herefrom at 130° C. in 2 min. and 50 sec.

EXAMPLE 3

15.4 g (0.1 mole) 1,2 cyclohexanedicarboxylic acid anhydride and 11.3 g (0.1 mole) ε-caprolactam were reacted for 4 hours at 125° C.

To the reaction product formed 100 g (0.05 mole) polyethylene glycol (molecular mass 2000) and 19.4 g (0.1 mole) diphenylcarbodiimide were subsequently added. After stirring for 2 hours at 125° C. the whole was cooled to 60° C. and the diphenylurea formed from the diphenylcarbodiimide was filtered off.

10 g of the product formed was dissolved at 100° C. in 13 g caprolactam. After addition of this solution to 0.4 g potassiumlactamate in 15.4 g caprolactam a solid nylon polymer was formed herefrom at 130° C. in 2 min. and 55 seconds.

EXAMPLE 4

10 g (0.1 mole) succinic acid anhydride and 11.3 g (0.1 mole) ε-caprolactam were reacted for 4 hours at 125° C.

To the reaction product formed 224 g (0.033 mole) Pluracol 380 (primary hydroxyl group terminated polyether triol, OH equivalent weight: 2244, BASF Wyandotte Corp.) and 19.4 g (0.1 mole) diphenylcarbodiimide were subsequently added. After stirring for 2 hours at 125° C. the whole was cooled to 60° C. and the diphenylurea formed from the diphenylcarbodiimide was filtered off. 12 g of the product formed was dissolved at 100° C. in 13 g caprolactam. After addition of this solution to 0.3 g sodiumlactamate in 15.4 g caprolactam a solid nylon polymer was formed herefrom at 130° C. in 3 min. and 25 seconds.

I claim:

1. Process for preparing an acyl-lactam compound comprising:

reacting the reaction product of a lactam with a dicarboxylic acid anhydride, said reaction product having the formula

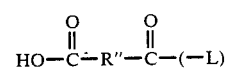

wherein

R″ is a bivalent radical having the following formula

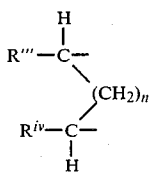

wherein
- R''' is H, alkyl, cycloalkyl, aryl, alkaryl or aralkyl,
- $R^{iv}$ is H, alkyl, cycloalkyl, aryl, alkaryl or aralkyl where
- R''' and $R^{iv}$ may jointly form a substituted or non-substituted cycloalkyl residue
- n is 0 or 1
- (-L) represents a non-opened lactam ring of the formula

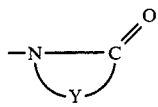

wherein Y has 3–11 carbon atoms with
a polyol having an equivalent weight of at least 300 up to 3,000 at a temperature of at most 150° C.

2. Process according to claim 1, wherein said polyol is selected from the group consisting of polyether polyols, polyester polyols, polybutadiene polyols, siloxane-containing polyols, polymeric polyols, and mixtures thereof.

3. Process according to claim 1, wherein said dicarboxylic acid anhydride is selected from the group consisting of glutaric acid anhydride, succinic acid anhydride and 1,2-cyclohexane-dicarboxylic acid anhydride.

4. A process for preparing an acyl lactam compound comprising:
(A) reacting a lactam selected from the group consisting of 2-pyrrolidone, 2-piperidone, enantholactam, decanolactam, undecanolactam, lauryllactam, caprolactam, and mixtures thereof with
a dicarboxylic acid anhydride selected from the group consisting of glutaric acid anhydride, succinic acid anhydride, and 1,2 cychohexanedicarboxylic acid anhydride
in the liquid state at a temperature of 70° C.–140° C. whereby a reaction product(s) is obtained;
(B) reacting the thus obtained reaction product(s) with a polyol having an equivalent weight of 300 up to 5,000 whereby the acyl lactam compound(s) is obtained.

5. The process according to claim 4 wherein an esterification catalyst is present in step (B).

* * * * *